(12) United States Patent
Racz

(10) Patent No.: US 9,480,800 B2
(45) Date of Patent: *Nov. 1, 2016

(54) NEURAL INJECTION SYSTEM AND RELATED METHODS

(71) Applicant: Custom Medical Applications, Farmers Branch, TX (US)

(72) Inventor: N. Sandor Racz, Coppell, TX (US)

(73) Assignee: Custom Medical Applications, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/089,029

(22) Filed: Apr. 1, 2016

(65) Prior Publication Data

US 2016/0213860 A1   Jul. 28, 2016

Related U.S. Application Data

(60) Continuation of application No. 11/508,416, filed on Oct. 7, 2014, now abandoned, which is a continuation of application No. 13/742,138, filed on Jan. 15, 2013, now Pat. No. 8,882,712, which is a division of application No. 12/956,551, filed on Nov. 30, 2010, now Pat. No. 8,377,005, which is a continuation of application No. 11/853,671, filed on Sep. 11, 2007, now Pat. No. 7,857,788.

(60) Provisional application No. 60/843,642, filed on Sep. 11, 2006.

(51) Int. Cl.
| | |
|---|---|
| *A61M 25/00* | (2006.01) |
| *A61M 5/32* | (2006.01) |
| *C07C 29/151* | (2006.01) |
| *A61B 17/34* | (2006.01) |
| *A61K 48/00* | (2006.01) |

(52) U.S. Cl.
CPC ........ *A61M 5/3291* (2013.01); *A61B 17/3403* (2013.01); *A61K 48/0075* (2013.01); *C07C 29/1512* (2013.01); *Y02P 20/544* (2015.11)

(58) Field of Classification Search
CPC .......... A61M 5/3291; A61M 25/007; A61M 25/0102
USPC .................... 604/158, 164.01, 264
See application file for complete search history.

(56) References Cited

U.S. PATENT DOCUMENTS

| | | |
|---|---|---|
| 2,922,420 A | 1/1960 | Cheng |
| 3,565,074 A | 2/1971 | Foti |

(Continued)

FOREIGN PATENT DOCUMENTS

| | | |
|---|---|---|
| JP | 201167553 | 4/2011 |

OTHER PUBLICATIONS

Examiner's Answer to Appeal Brief dated Dec. 20, 2010, in U.S. Appl. No. 12/139,233.

(Continued)

*Primary Examiner* — Gerald Landry, II
(74) *Attorney, Agent, or Firm* — Ramey & Schwaller, LLP

(57) ABSTRACT

A novel neural injection system and related methods are herein disclosed. Various embodiments of an embodiment of a neural injection system of the present invention provide for at least one benefit of enhanced injection characteristics, increased operational efficiency, reduced cost per unit, reduced incidence of injury through intraneural/intravascular injection, reduced incidence of injury through pricking/piercing, and/or the like.

13 Claims, 3 Drawing Sheets

(56) References Cited

U.S. PATENT DOCUMENTS

| | | | |
|---|---|---|---|
| 3,856,009 | A | 12/1974 | Winnie |
| 4,230,123 | A | 10/1980 | Hawkins, Jr. |
| 4,308,875 | A | 1/1982 | Young |
| 4,317,445 | A | 3/1982 | Robinson |
| 4,629,450 | A | 12/1986 | Suzuki |
| 4,781,692 | A | 11/1988 | Jagger |
| 4,909,793 | A | 3/1990 | Vining |
| 4,924,881 | A | 5/1990 | Brewer |
| 4,944,724 | A | 7/1990 | Goldberg et al. |
| 4,967,766 | A | 11/1990 | Bradshaw |
| 4,973,313 | A | 11/1990 | Katsaros |
| 4,994,034 | A | 2/1991 | Botich |
| 5,002,535 | A * | 3/1991 | Gross ............... A61B 17/3401 604/272 |
| 5,012,818 | A * | 5/1991 | Joishy ............... A61B 10/0045 600/567 |
| 5,106,376 | A | 4/1992 | Mononen |
| 5,129,404 | A | 7/1992 | Spehr |
| 5,228,455 | A | 7/1993 | Barcel |
| 5,242,410 | A | 9/1993 | Melker |
| 5,250,035 | A | 10/1993 | Smith |
| 5,304,141 | A | 4/1994 | Johnson |
| 5,312,360 | A | 5/1994 | Behl |
| 5,336,191 | A | 8/1994 | Davis |
| 5,344,439 | A | 9/1994 | Otten |
| 5,466,225 | A | 11/1995 | Davis |
| 5,470,327 | A * | 11/1995 | Helgren ............... A61J 1/2089 604/411 |
| 5,480,389 | A | 1/1996 | McWha |
| 5,571,091 | A | 11/1996 | Davis |
| 5,573,519 | A | 11/1996 | Zohmann |
| 5,628,734 | A | 5/1997 | Hatfalvi |
| 5,669,882 | A | 9/1997 | Pyles |
| 5,730,749 | A | 3/1998 | Battenfield |
| 5,800,407 | A | 9/1998 | Eldor |
| 5,800,445 | A | 9/1998 | Ratcliff |
| 5,817,074 | A * | 10/1998 | Racz ............... A61B 17/3401 604/264 |
| 5,836,914 | A * | 11/1998 | Houghton ........... A61B 17/3401 604/117 |
| 5,865,806 | A | 2/1999 | Howell |
| 5,871,470 | A | 2/1999 | McWha |
| 6,345,044 | B1 | 2/2002 | Edgar, III |
| 6,383,145 | B1 | 5/2002 | Worm |
| 6,387,163 | B1 | 5/2002 | Leong |
| 6,447,477 | B2 * | 9/2002 | Burney ............... A61B 10/0233 604/158 |
| 6,547,769 | B2 | 4/2003 | VanTassel |
| 6,551,253 | B2 | 4/2003 | Worm |
| 6,558,353 | B2 | 5/2003 | Zohmann |
| 6,689,142 | B1 | 2/2004 | Tremaglio, Jr. et al. |
| 6,855,132 | B2 | 2/2005 | VanTassel |
| 6,949,087 | B2 | 9/2005 | VanTassel |
| 6,968,238 | B1 | 11/2005 | Kuzma |
| 8,449,503 | B2 | 5/2013 | Racz |
| 2002/0123723 | A1 * | 9/2002 | Sorenson ............... A61M 25/06 604/164.01 |
| 2003/0130621 | A1 | 7/2003 | Bryan et al. |
| 2003/0161824 | A1 * | 8/2003 | Rackley ............... A61M 5/3286 424/125 |
| 2004/0254541 | A1 * | 12/2004 | Wong ............... A61M 5/158 604/239 |
| 2005/0234390 | A1 * | 10/2005 | Buckman ........... A61B 17/3415 604/22 |
| 2006/0206055 | A1 * | 9/2006 | Ice ............... A61B 17/3401 604/164.01 |
| 2007/0255230 | A1 * | 11/2007 | Gross ............... A61B 17/8811 604/272 |
| 2008/0065018 | A1 | 3/2008 | Racz |

OTHER PUBLICATIONS

Office Action dated Jul. 13, 2015, issued in Korean patent application No. 2014-31076.
Office Action dated Feb. 24, 2015, issued in Japanese patent application 2014-051487.
James Heavner et al., Sharp Versus Blunt Needle: A Comparative Study of Penetration of Internal Structures and Bleeding in Dogs, Pain Practice, Sep. 2003, 226-231, 3-3.
Final Office Action from United States Patent and Trademark Office dated Oct. 29, 2010, in U.S. Appl. No. 11/853,785.
Non-Final Office Action from United States Patent and Trademark Office dated Jul. 15, 2010, in U.S. Appl. No. 11/853,785.
Final Office Action from United States Patent and Trademark Office dated Mar. 9, 2010, in U.S. Appl. No. 11/853,785.
Non-Final Office Action from United States Patent and Trademark Office dated Sep. 29, 2009, in U.S. Appl. No. 11/853,785.
Final Office Action from United States Patent and Trademark Office dated Jun. 15, 2009, in U.S. Appl. No. 11/853,785.
Non-Final Office Action from United States Patent and Trademark Office dated Nov. 7, 2008, in U.S. Appl. No. 11/853,785.
Final Office Action from United States Patent and Trademark Office dated Mar. 22, 2010, in U.S. Appl. No. 12/139,233.
Non-Final Office Action from United States Patent and Trademark Office dated Jun. 8, 2009, in U.S. Appl. No. 12/139,233.
Final Office Action from United States Patent and Trademark Office dated May 27, 2010, in U.S. Appl. No. 11/853,671.
Non-Final Office Action from United States Patent and Trademark Office dated Nov. 12, 2009, in U.S. Appl. No. 11/853,671.
Final Office Action from United States Patent and Trademark Office dated Jul. 22, 2009, in U.S. Appl. No. 11/853,671.
Non-Final Office Action from United States Patent and Trademark Office dated Mar. 6, 2009, in U.S. Appl. No. 11/853,671.
Extended European Search Report dated May 9, 2014, in European Application No. 14160297.9.

* cited by examiner

NEURAL INJECTION SYSTEM AND RELATED METHODS

RELATED APPLICATIONS

This application claims priority to U.S. Provisional Application No. 60/843,642 filed Sep. 11, 2006, and is a continuation application of U.S. Non provisional application Ser. No. 11/508,416, filed Oct. 7, 2014 and issued as U.S. Pat. No. 9,302,072 on Apr. 5, 2016, and is a continuation application of U.S. Non provisional application Ser. No. 13/742,138 filed Jan. 15, 2013 and issued as U.S. Pat. No. 8,882,712 on Nov. 11, 2014, which is a divisional application of U.S. Non provisional application Ser. No. 12/956,551 filed Nov. 30, 2010 and issued as U.S. Pat. No. 8,377,005, which is a continuation of U.S. Non provisional application Ser. No. 11/853,671 filed Sep. 11, 2007 and issued as U.S. Pat. No. 7,857,788 on Dec. 28, 2010, all incorporated by reference.

SUMMARY OF THE INVENTION

Endoscopic surgery is widely practiced throughout the world today and its acceptance is growing rapidly. In general, endoscopic surgery involves one or more incisions made by trocars (cannulae carrying sharp obturators) where the cannulae are left in place to provide instrument ports so that endoscopic surgical instruments may be inserted into the body. An endoscope is often inserted through one cannula, while a cutter, dissector, or other surgical instrument is inserted through another cannula for purposes of manipulating and/or cutting an internal organ. Sometimes it is desirable to have several cannulae in place at once in order to receive several surgical instruments. In this manner, organs or tissue may be grasped with one surgical instrument, and simultaneously may be cut with another surgical instrument, all under view of the surgeon via the endoscope. In order to enlarge the closed space surrounding the surgical site, a pneumoneedle (or Veress needle) is inserted into the body cavity and the cavity is insufflated by injecting gas (typically C0 into the cavity through the Veress needle). At the conclusion of the procedure, the body cavity is desufflated (aspirated) by opening a valve on one or more trocar cannulae.

A very successful embodiment of a needle with an opening at the distal end portion and with a side port is disclosed in U.S. Pat. No. 5,817,074 ("the '074 patent"). The '074 patent discloses a stellate ganglion sympathetic block needle having a side port positioned at a predetermined distance from the needle distal. The stellate ganglion sympathetic block needle allows for an effective stellate ganglion sympathetic block even if the needle is placed such that the needle distal opening is under the anterior longitudinal ligament, which results in the needle distal opening being constricted, thereby interfering with the injection of the anesthesia. When this interference occurs, the side port of the novel stellate ganglion sympathetic block needle allows directional injection onto the surface of the anterior longitudinal ligament in order to spread onto the surface of the longus coli muscle toward the stellate ganglion, thereby achieving an effective stellate ganglion sympathetic block. This invention has found wide applicability, however, certain procedures might prefer or require a blunt needle without an opening at the distal end portion.

It is known to have needles with a blocked tip (distal end) and with a side opening, Such needles are used for procedures such as thoracentesis, which involves inserting the needle through the thoracic cage into the pleural space between the lung and the chest wall to draw off fluid for diagnostic or therapeutic purposes. Thoracentesis needles generally consist of an orifice free, sharp conical end and a circular side hole for draining fluid.

U.S. Pat. No. 5,573,519 discloses an elongated, hollow spinal needle having a modified, pencil-like point with a rounded shoulder at the juncture between the modified, pencil-like point and the body of the spinal needle. A side port formed in the hollow needle is adjacent the rounded shoulder, extending from the rounded shoulder. Further, the leading edge of the side port is located not more than 1.5 times the external diameter of the hollow needle from the tip (distal end) of the pencil-like point to reduce the potential bending moment between the tip and the side port. The cross sectional area of the side port is configured to be about equal to the cross sectional area of the lumen of the hollow needle.

U.S. Pat. No. 5,800,407 discloses an epidural catheter that purportedly combines the benefits of the open-end and closed-end three lateral holes type catheters. The epidural catheter is stated as being designed to include an end hole and a plurality of lateral holes. The combined end and multiple lateral holed epidural catheter of the present invention includes seven holes within a 1.5 cm head. The holes are positioned along the head such that one hole is provided at the tip, three lateral holes are circumferentially arranged about the head at approximately 1 mm from each other, and three additional holes are axially displaced from one another by approximately 4 mm. All the holes are within the 1.5 cm from the tip. The radius of each of the lateral holes is the same, thus, the anesthetic solution stream is the same from each hole.

Further, needles with retractable stylets and/or blades have been long known in the art. For example, U.S. Pat. No. 4,909,793 (the '793 patent) discloses an intravenous catheter apparatus having a retractable stylet, comprising a cannula member positioned at the end of a catheter, affixed to an end portion of a stylet body and engaged to an end portion of a tubular stylet protector chamber. The stylet protector chamber of the '793 patent includes a stylet body plunger member having a stylet body and stylet on the distal end thereof, the stylet insertable in the bore of the cannula, and extending past the distal end of the cannula when the stylet is in the full extended position.

U.S. Pat. No. 4,924,881 discloses an implantable endocardial lead with retractable fixation device. The fixation device comprises a sharpened helix which can be repeatedly both retracted within a distal end of the lead and displaced outside the lead. A threaded stylet passes through a lumen from a proximal end of the lead to the distal end of the lead, where the threaded stylet is screwed into a piston supporting the helix. When the helix is in an exposed position, torque can be transmitted from the proximal end of the lead through the distal end to the piston and thence to the helix to screw the helix into the endocardial tissue.

U.S. Pat. No. 4,967,766 discloses an implantable endocardial lead with retractable fixation apparatus. The fixation apparatus comprises a sharpened helix that can be repeatedly both retracted within an electrode at a distal end of the lead and displaced outside the electrode by action of a flexible, tubular lanyard. The lanyard passes through a lumen from a proximal end of the lead to the distal end of the lead, where the lanyard is attached to a piston supporting the helix. At the proximal end of the lead, a jig moves the lanyard with respect to a longitudinal axis of the lead. When the helix is in an exposed position, torque can be transmitted from the proximal end of the lead to the distal end thereof, through the electrode to the piston and then to the helix to screw the helix into the endocardial tissue. To stiffen the lead during implantation, a stylet can be inserted into a lumen in the lanyard.

U.S. Pat. No. 5,129,404 discloses an implantable endocardial lead with retractable sharpened helix. The piston has a central bore for receiving a specialized stylet. The stylet comprises a flexible wire having an enlarged distal end or tip. An elastomeric sliding sleeve fits over the wire. When the proximal end of the stylet is inserted into the bore in the piston, the wire can be withdrawn slightly, pulling the enlarged tip into the tube, and wedging the tube against the walls of the bore. By manipulating the stylet, the helix can be exposed outside of the lead, or retractable into the lead, as desired.

U.S. Pat. No. 5,228,455 discloses an implant tool for use with an endocardial or other implantable lead having an extendable/retractable positive fixation tip including a hollow cylindrical housing and a custom designed stylet. The cylindrical housing attaches to a proximal end of the implantable lead. The stylet is inserted through the implant tool and into a lumen of the lead. The presence of the stylet, made from a length of relatively stiff wire, helps guide the distal tip of the lead to a desired implant location. The cylindrical housing includes a body portion and an end portion. The end portion is rotatable relative to the body portion. The stylet includes a knob on its proximal end, and also includes a stub pin slightly forward of its proximal end. The stub pin is received within a slot along the side of the cylindrical housing. Two spaced-apart recesses along the length of the slot allow the stub pin to be respectively held therein. When the stub pin is held in a first recess, the stylet wire has advanced sufficiently far into the lead to facilitate implantation of the lead, but retains the positive fixation tip in its retracted position. When the stub pin is locked in a second recess, the stylet wire has advanced sufficiently far into the lead to engage the positive fixation tip and move it to its extended position. A method of using the implant tool is also disclosed.

U.S. Pat. No. 5,344,439 discloses a catheter with a retractable anchor mechanism for providing drugs and/or electrical stimulation to the human body. The catheter has a flexible tubular casing consisting of an outer member and an inner member which enclose at least one lumen. The retractable anchor mechanism is located near the distal end of the catheter and is moveable from a first extended position to a second retracted position. A capture member is connected to the anchor mechanism. The capture member has a socket portion and a necked down portion for guiding the enlarged tip of a stylet into the socket portion for releasable engagement therewith. The anchor mechanism is moved from the first extended position to the second retracted position by inserting a stylet and applying pressure in the distal direction and is moved from the second retracted position to the first extended position by partially withdrawing the stylet thereby applying pressure in the proximal direction. The anchor mechanism consists of a plurality of lobes in one embodiment and of a continuous diaphragm in another.

Further examples of retractable stylets and/or cutting portions include, but are not limited to, U.S. Pat. No. 4,781,692; U.S. Pat. No. 4,909,793; U.S. Pat. No. 6,383,145; U.S. Pat. No. 6,551,253; and U.S. Pat. No. 6,968,238.

However, none of these prior art solutions significantly reduce a risk of injury from a sharp blade and/or edge of an injection system or provide an enhanced medical instrument for neural injection.

Therefore, it would be advantageous to design a needle/neural injection system, which can effectively inject a medicament with less concern for an intraneural and/or an intravascular injection.

Accordingly, various embodiments of the present invention comprise a neural injection system comprising an at least partially hollow cannula being defined by a first inside diameter, a first outside diameter, and a first length, and a side port located coaxially along the cannula for fluid communication from inside said at least partially hollow cannula to outside said at least partially cannula, wherein said cannula has a rounded open blunt distal end; and a stylet, wherein the stylet is capable of being releasably locked in a first position within said cannula. Further embodiments comprise an introducer, the introducer being defined by a second inside diameter, a second outside diameter, and a second length, wherein the said second inside diameter is larger than said first outside diameter, wherein the introducer is used for access across a tissue of a patient that cannot be punctured by the rounded open blunt distal end during a normal insertion procedure. Various embodiments of the present invention provide for at least one benefit of enhanced injection characteristics, increased operational efficiency, reduced cost per unit, reduced incidence of injury through intraneural/intravascular injection, reduced incidence of injury through pricking/piercing, and/or the like.

Various embodiments of the present invention further comprise methods of use. In an exemplary, non-limiting embodiment of a method of the present invention wherein a patient is in need of treatment by a medicament, the method comprises the steps of placing the patient in a supine position and/or extended position; locating a site for injection; inserting at least a portion of the blunt needle into the site; and injecting the medicament into the patient. Further embodiments comprise stimulating the site and/or ablating the site.

In further embodiments, the patient is in need of access to a particular tissue.

In various other embodiments, the invention's blunt surgical needle and/or blunt surgical assemblage is ideally suited for injection into tissue of medicaments containing nucleic acid encoding a therapeutic agent (or cells containing such nucleic acid), For example, the invention needle (when attached to an appropriate catheter) or invention surgical assemblage can be used to inject medicament(s) into the wall of a beating heart or other internal organ, without substantial loss of the medicament at the surface of the body wall and without substantial damage to tissue at the injection site caused by injectate.

BRIEF DESCRIPTION OF THE FIGURES

In order that the manner in which the above-recited and other enhancements and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE INVENTION

Figure 1:
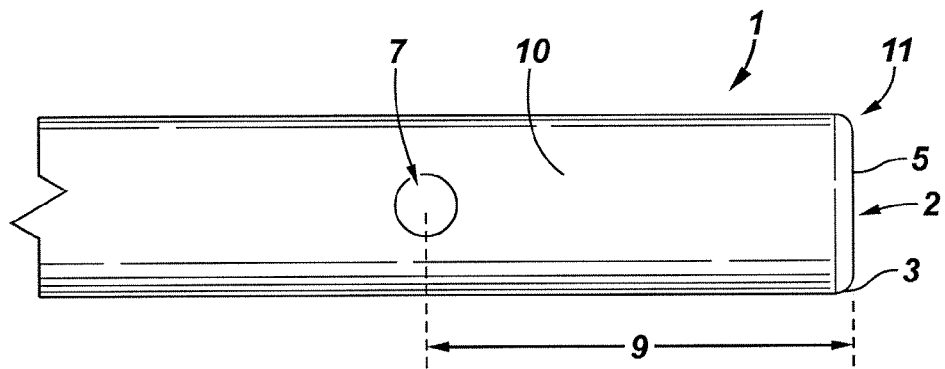
FIG. 1 is an illustration of a distal portion of a blunt needle of an embodiment of a neural injection system of the present invention.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

As used herein the term, "air" means and refers to a gaseous mixture that comprises at least about 20 mole percent O2, As used herein, the term "attached," or any conjugation thereof describes and refers to the at least partial connection of two items.

Exemplary, non-limiting embodiments of medical instrument, neural injection systems, and/or the like that can be modified according to various teachings of the present invention include, but are not limited to, U.S. Pat. No. 6,949,087; U.S. Pat. No. 6,855,132; U.S. Pat. No. 6,558,353; U.S. Pat. No. 6,547,769; U.S. Pat. No. 6,387,163; U.S. Pat. No. 6,245,044; U.S. Pat. No. 5,871,470; U.S. Pat. No. 5,865,806; U.S. Pat. No. 5,836,914; U.S. Pat. No. 5,817,074; U.S. Pat. No. 5,800,445; U.S. Pat. No. 5,730,749; U.S. Pat. No. 5,669,882; U.S. Pat. No. 5,628,734; U.S. Pat. No. 5,573,519; U.S. Pat. No. 5,571,091; U.S. Pat. No. 5,480,389; U.S. Pat. No. 5,466,225; U.S. Pat. No. 5,336,191; U.S. Pat. No. 5,312,360; U.S. Pat. No. 5,304,141; U.S. Pat. No. 5,250,035; U.S. Pat. No. 5,242,410; U.S. Pat. No. 5,106,376; U.S. Pat. No. 4,994,034; U.S. Pat. No. 4,973,313; U.S. Pat. No. 4,629,450; U.S. Pat. No. 4,317,445; U.S. Pat. No. 4,308,875; U.S. Pat. No. 4,230,123; U.S. Pat. No. 3,856,009; U.S. Pat. No. 3,565,074; and, U.S. Pat. No. 2,922,420, the contents of which are hereby incorporated by reference as if they were presented herein in their entirety. In general, any catheter may be used with the various embodiments of the present invention.

As used herein, the term "CO" means and refers to carbon dioxide in any form, i.e., gas or liquid.

As used herein, the term "fixation apparatus" means and refers to an apparatus for connecting to and at least partially rigidly supporting fixation structure further including a support for rigidly connecting the cast to the frame and biasing structure operable between the head and the frame and/or the fixation structure to bias the cast into positive contact with the upper teeth and/or palate. The apparatus is used in stereotatic diagnosis and treatment.

As used herein, a "fluid" is a continuous, amorphous substance whose molecules move freely past one another and that has the tendency to assume the shape of its container, for example, a liquid or a gas.

As used herein, the term "medicament(s)" means and refers to all types of fluidic substances that have a beneficial, desired or therapeutic effect. Non-limiting examples of medicaments suitable for use in the invention methods include anesthesia, biologically active agents, such as small molecule drugs, proteinaceous substances, polynucleotides or nucleic acids (e.g. heterologous DNA, or RNA) and vectors, liposomes, and the like, containing such nucleic acids or polynucleotides, as well as liquid preparations or formulations thereof.

As used herein, the term "medical instrument" means and refers to any item, instrument or structure capable of connecting to a catheter, such as, but not limited to a stimulation device, tubing, piping, a medicament delivery system, a meter, a liquid repository (such as an I.V. bag), a syringe, and/or the like.

As used herein, the term "normal insertion procedure" means and refers to a typical surgical and/or insertion procedure as disclosed in Heavner et al., "Sharp Versus Blunt Needle: A Comparative Study of Penetration of Internal Structures and Bleeding in Dogs", 2003, World Institute of Pain, Pain Practice, 3:3, 226-231.

As used herein, the term "stylet" means and refers to a small poniard. Stylets of the present invention are capable of being hollow, but such is not required.

Other than in the operating examples, or where otherwise indicated, all numbers expressing quantities of ingredients or reaction conditions used herein are to be understood as modified in all instances by the term "about".

In general, various embodiments of a device of the present invention comprise neural injection and/or treatment systems and related methods with at least one benefit of enhanced injection characteristics, increased operational efficiency, reduced cost per unit, reduced incidence of injury through intraneural/intravascular injection, reduced incidence of injury through pricking/piercing, and/or the like.

More particularly, embodiments of the present invention generally comprise a neural injection system comprising an at least partially hollow cannula being defined by a first inside diameter, a first outside diameter, and a first length, and a side port located coaxially along the cannula for fluid communication from inside said at least partially hollow cannula to outside said at least partially hollow cannula, wherein said cannula has a rounded open blunt distal end; a stylet, wherein the stylet is capable of being releasably locked in a first position within said cannula; and, an introducer being defined by a second inside diameter, a second outside diameter, and a second length, wherein the introducer is used for access across a tissue of a patient that cannot be punctured by the rounded open blunt distal end during a normal insertion procedure. In further embodiments, the neural injection system further comprises a medical instrument, i.e., any item, instrument or structure capable of connecting to a connector, such as, but not limited to a stimulation device, tubing, piping, a medicament delivery system, a meter, a liquid repository (such as an I.V. bag), a syringe, and/or the like connected to the connector end.

Various embodiments of the invention methods and devices are designed for injection of minute amounts of fluid medicaments into tissue or a body wall, for example, an interior body wall. The therapeutic amount of the medicament to be administered according to the invention method will vary depending upon the therapeutic goal to be accomplished, the size and age of the subject, the pharmacokinetics of the injectate, and the like. However, a therapeutic amount according to the present invention is typically in the range from about 0.1 cc to about 5.0 cc.

Various other embodiments are designed for treatment of a target tissue(s). In an embodiment, treatment of a tissue comprises at least one of probing, ablation, stimulating, and/or the like. In general, treatments capable with various embodiments of the present invention can be any treatment common in the art and should not be limited by the present disclosure.

A cannula associated with various embodiments of a neural injection system is generally a cylindrical structure extending from a proximal end to a distal end. In an embodiment, the cannula is of a generally constant circumference. The cannula is capable of being differentiated by an inside diameter and an outside diameter. In an embodiment, an outside diameter is between about 0.0355 to about 0.03600 mm and an inside diameter is between about 0.0230 to about 0.0245 mm. In an alternate embodiment, an outside diameter is between about 0.0205 to 0.280 mm and an inside diameter between about 0.0155 to 0.0170 mm. Generally, an inside diameter and an outside diameter are capable of being any desired length and any particular length should not be construed as a limitation on the scope of the appended claims.

In an embodiment of the present invention, a tip end or distal end of the at least partially hollow cannula comprises a rounded portion, such as a shoulder, about the end of the first length, generally extending circumferentially around the cannula. In an embodiment, the rounded portion is smooth. In an alternate embodiment, the portion is at least partially roughened. In an alternate embodiment, at least one generally beveled edge extends along the portion. In an embodiment of a portion with a bevel, the beveled edge extends circumferentially about the shoulder whereby the point of the tip is still capable of being inserted into at least one tissue of a patient, but the exposed edge or point is not as sharp as a needle point.

In an embodiment, a connector is about the proximal end of the cannula. A connector of the present invention comprises an attachment means for attaching the cannula and an optional further medical instrument. The connection or connections at the connector end may be any type of connection common in the art, such, as for example, and not by way of limitation, a luer lock connector, a threaded attachment, an interference fit attachment, a clamp, a system utilizing a dowel, two or more of the aforesaid in combination, and/or the like.

A stylet of various embodiments of the present invention generally extends through at least a portion of the hollow portion of the cannula. In an embodiment, a stylet of the present invention is generally characterized by an outside diameter and a length extending from a proximal end to a distal end, wherein the outside diameter is smaller than the first inside diameter of the cannula. In various embodiments, the stylet comprises a side port and is at least partially hollow. In an embodiment, the stylet and the cannula define a passageway for passage of at least one medicament.

In general, various embodiments of stylets of the present invention are capable of being inserted to any desired location within the cannula. In an embodiment, the distal end of the stylet is flush with the shoulder of the distal end of the cannula. In an alternate embodiment, the distal end of the stylet extends past the shoulder of the distal end of the cannula. In an alternate embodiment, the shoulder of the distal end of the cannula extends past the distal end of the stylet. Various embodiments of the present invention either fixedly connect, releasably connect, or leaves unconnected the stylet and the cannula. Accordingly, in an embodiment, the stylet is capable of sliding within the cannula. In an alternate embodiment, the stylet is releasably secured within the cannula by a locking mechanism, such as, but not limited to a luer lock, an interference fit, a snap, screw threads, and/or the like. In an embodiment of a luer lock system, internal male luer threads are located in or about the stylet adjacent to receive and engage a cannula having female luer threads thereon. In alternate embodiments, the luer lock is reversed. In an alternate embodiment, the cannula is welded to or otherwise fixedly connected to the cannula.

A side port of the present invention is generally a port extending from the exterior of the cannula to the interior of the cannula and/or stylet. The shape of the side port can vary. In an embodiment, a port is circular. In an alternate embodiment, a port is ovular. In an alternate embodiment, a port is a quadrangular port, such as a rectangle or a square. In an alternate embodiment, the port is triangular. In general, ports of the present invention can be any shape sufficient to permit fluid aspiration therethrough.

A side port of the present invention may be further characterized by the associated edge of the port on the cannula and/or stylet. In an embodiment, a port has a slightly inwardly beveled edge extending from the exterior surface of the cannula to the interior surface. In an alternate embodiment, a port has a slightly outwardly beveled edge extending from the interior surface of the cannula to the exterior surface. In an embodiment, the degree of bevel can be used to change the pressure of the medicament as it enters the target tissue; facilitate a change in the degree of spread of the medicament; and, allow for a smooth surface as the cannula is inserted to the target tissue.

Further embodiments of the present invention comprise a cannula and/or stylet with multiple ports arranged in any orientation about the shaft. Further embodiments comprise a porous portion, such that the port is one of multiple ports and a medicament introduced into the neural injection system would tend to ooze out of the cannula into the target tissue. Accordingly, an embodiment comprises a blunt cannula with a weeping tip portion for microinjection of medicaments into a tissue.

In an embodiment, the neural injection system comprises a nonporous hollow cannula having a connector end adapted to mate with a neural injection system, a porous distal end in fluid-tight connection to the cannula, and a closed distal portion. The porous distal end of the neural injection system is adapted to cause a liquid injectate to weep or ooze therefrom multidirectionally under injection pressure while the distal portion is inserted into a tissue. In an embodiment, the porous distal end oozes at a substantially uniform rate.

In an embodiment, a stylet comprises, in application, a side port across a cannula and a side port across the stylet. In various embodiments, the side ports are positioned such that reasonable alignment of the side ports occurs at a desired position of the stylet within the cannula such that a medicament may pass from across the reasonably aligned side ports.

Certain tissues in a patient's body require an introducer to make a slit and/or hole prior to insertion of a novel blunt cannula of the present invention. In an embodiment, a separate introducer is included, the introducer being defined by a second inside diameter, a second outside diameter, and a second length, wherein the said second inside diameter is larger than said first outside diameter, wherein the introducer is used for access across a tissue of a patient that cannot be punctured by the rounded open blunt distal end during a normal insertion procedure and wherein the second inside diameter is larger than the first outside diameter.

In an embodiment, the introducer is integral with a neural injection system of the present invention. In an embodiment, an introducer is positioned surrounding a cannula and is slidable from within about a body of a neural injection system to engage a patient's tissue. Typically in such an embodiment, the introducer slides from the neural injection system to a position past a distal end of the cannula to engage a tissue of the patient. In an embodiment, the introducer is maintained within a housing of the neural injection system such that the distal portion of the introducer is only exposed during a procedure requiring the introducer to puncture a tissue, thereby minimizing the injuries resulting from prior art exposed introducers.

In embodiments where the introducer is a portion of the neural injection system, the introducer can be extended by various methods, such as, but not limited to physical means, pneumatic means, mechanical means, hydraulic means, electronic means, and/or the like. Generally, any method of extending a medical instrument can be used. Typically, the same method used for extension is capable of being used for retraction of the introducer. In preferred embodiments, the introducer is maintained in relation to the cannula such that no exposed sharp edge(s) of the introducer is capable of being contacted by a user, thereby minimizing accidental punctures and/or pricks by the introducer.

In yet an alternate embodiment, the introducer is positioned inside or within the cannula, thereby creating a slit in the tissue slightly smaller than the cannula, but minimizing the hole and trauma to the patient's tissue.

In various embodiments, the size of the neural injection system is important. To minimize size, an introducer is capable of being a separate medical instrument. Alternately, to minimize size and reduce the need for multiple medical instruments, a stylet can be used as an introducer.

Accordingly, in various embodiments, at least a portion of a stylet is edged, such that at least a portion of the distal edge of the stylet is capable of penetrating a tissue that a normal insertion procedure could not penetrate. In an embodiment, the distal end of the stylet has at least one bevel. In an alternate embodiment, the distal end of the stylet is a point. Generally, in embodiments characterized as such, at least a portion of the distal end of the stylet can be of any shape capable of penetrating a tissue that a normal insertion procedure could not penetrate.

Embodiments of connectors of the present invention optionally further comprise at least one wing. A wing of the present invention may be any structure. In an embodiment, the wing is an extension of the connector, such as, but not limited to, a rigid flap, a rigid bar, a flexible flap, a flexible bar, and/or the like. In further embodiments, at least two wings extend from about the connector, such as, for example, and not by way of limitation, two wings extending evenly spaced circumferentially about the connector. Further embodiments have various numbers of wings extending from, attached to, or secured to the connector in various arrangements.

In an embodiment, one wing extends from about a proximal end of a cannula. A single wing connector or hub has certain benefits that are appealing for a variety of applications. It is common in the medical field that neural injection systems are inserted into patients for a variety of procedures. An issue that arises is how to secure or stabilize the neural injection system before, during and/or after insertion. A hemostat, pliers, and/or the like are often used to secure an area about the connector to secure it, However, the use of a hemostat, pliers, and/or the like is capable of occluding visualization down and/or about the needle and/or catheter. Further, the use of any metal tends to degrade the quality of images produced through NMR, X-ray, and/or the like. As well, the use of an instrument to secure the needle that is capable of interfering with an image through or about the needle is not desired in many applications. Accordingly, numerous procedures, such as, but not limited to fluoroscopic guidance procedures, NMR procedures, X-ray procedures, direct viewing procedures, and/or the like would find a benefit in a single winged structure. Solutions in the art comprise attaching wings to the connector, in most cases, two wings. However, the inventors are unaware of the art field containing a neural injection system comprising an elongated at least partially hollow shaft comprising a sharp needle at least partially occluded, closed distal end; a connector end; and, at least one side port located coaxially along the shaft, with a single wing. Double winged structures exist in the art, but are more expensive to manufacture and the double wings do not add appreciable stability. Accordingly, benefits can be realized with a one winged design that can be secured by a hemostat, pliers and or the like, without requiring bending or manipulation of the needle and/or any associated connector and/or wing.

The inventor believes that the double winged structures were created so that, among other attributes, medical personnel could stabilize the needle by pinching the two wings together as the needle is inserted. However, pinching the two wings together creates inherent instability.

Various embodiments of the present invention further comprise a wire or other means of conveying stimulation to a target tissue. In an embodiment, the wire extends along the cannula from about the proximal end to the shoulder. In an alternate embodiment, the wire is integral (attached to) with the cannula. In an alternate embodiment, the wire extends along the outside of the cannula. In yet an alternate embodiment, a wire extends, along, through, and is integral with the stylet. No matter where the wire is contained or attached, it is preferable to have the wire secured so that the wire is not loose.

Design considerations that are capable of being implemented with various embodiments of the present invention include, but are not limited to designing the wire and connector such that they may be utilized as a plug and use type of arrangement. A plug and use arrangement is beneficial because it reduces the complexity of the device and reduces loose wires. In an embodiment, the wire is formed into the connector such that when the connector is connected to another medical instrument, the wire is able to communicate with the instrument. However, any connection common in the art that would allow the wire to communicate with a medical instrument is contemplated within the various embodiments of the present invention.

Further modifications of embodiments of a neural injection system with a wire comprise the introduction of insulation or at least one form insulation about the cannula, stylet, and/or wire. In general any method of insulation could be used such as, but not limited to, a plastic, a metal, and/or the like.

Further modifications of embodiments of a neural injection system with a wire comprise the introduction of a probe about the shaft and/or wire. In general any method of insulation could be used as described previously. Various probes capable of use with embodiments of the present invention include temperature probes, stimulation probes, cameras, and/or the like.

Accordingly, a further embodiment of the present invention comprises a neural injection system comprising an at least partially hollow cannula being defined by a first inside diameter, a first outside diameter, and a first length, and a side port located coaxially along the cannula for fluid communication from inside said at least partially hollow cannula to outside said at least partially cannula, wherein said cannula has a rounded open blunt distal end; a stylet, wherein the stylet is capable of being releasably locked in a first position within said cannula; and, an introducer being defined by a second inside diameter, a second outside diameter, and a second length, wherein the introducer is used for access across a tissue of a patient that cannot be punctured by the rounded open blunt distal end during a normal insertion procedure; and, a connector end connected through a connection to an instrument.

Also contemplated in various embodiments of the present invention are methods of use and manufacture of a neural injection system of the present invention.

An exemplary embodiment of a method of the present invention comprises a method for administering a medicament to a patient comprising the steps of locating a site for injection; inserting at least a portion of a neural injection system into the site, the neural injection system comprising an at least partially hollow cannula being defined by a first inside diameter, a first outside diameter, and a first length, and a side port located coaxially along the cannula for fluid communication from inside said at least partially hollow cannula to outside said at least partially hollow cannula, wherein said cannula has a rounded open blunt distal end; a stylet, wherein the stylet is capable of being releasably locked in a first position within said cannula; and, injecting the medicament into the patient. In an embodiment, the medicament is anesthesia. Further embodiments comprise the use of an introducer, the introducer being defined by a second inside diameter, a second outside diameter, and a second length, wherein the introducer is used for access across a tissue of a patient that cannot be punctured by the rounded open blunt distal end during a normal insertion procedure.

Further embodiments of a method of the present invention further comprise stimulating a tissue. Yet further embodiments of a method of the present invention comprise ablating at least a portion of the tissue about a site. Other embodiments comprise probing a tissue. And yet further embodiments of a method of the present invention comprise preparing a patient for administering a medicament.

In an embodiment of an administration of a block, such as a nerve block, the method further comprises preparing the patient. In an embodiment, preparing the patient comprises placing a patient in a supine position or extended position, without a pillow, with the patient's head in a neutral position.

In an embodiment of administration of a medicament, while standing on the side of the body that is to be blocked, the physician tactilely locates the cricoid cartilage. The neural injection system is then inserted in a position approximately one finger breadth below the cricoid cartilage, between the carotid sheath and the trachea on the side to be blocked, while aiming slightly medially until bony contact is made with the ventral lateral side of the body of the seventh cervical vertebra. When the neural injection system is in said position, the anesthesia is injected. The new design allows for directional injection out the side port onto the surface of the anterior longitudinal ligament. This allows the anesthesia to spread onto the surface of the longus coli muscle toward the stellate ganglion. Thus, an injection via the side port will achieve an effective stellate ganglion sympathetic block.

In another embodiment according to the present invention, there are provided methods for injecting a medicament into tissue in a subject in need thereof. The invention injection method comprises inserting the distal portion of an embodiment of the neural injection system into the tissue of the subject and causing a therapeutic amount of the medicament to ooze multidirectionally from a distal end into the tissue without substantial leakage or loss of the medicament at the surface of the tissue. The invention method using the invention with a porous distal end is designed for injection of minute amounts of fluid into tissue or a body wall, hence the use of the term "microinjection" herein. However, other amounts may also be injected.

In an alternate embodiment according to the present invention, there are provided methods for injecting a medicament into a subject in need thereof comprising inserting the distal portion of the neural injection system into an interior body wall or tissue of the subject and applying sufficient pressure to a liquid medicament in fluid communication with the distal portion of the neural injection system to expel the medicament such that the medicament weeps multidirectionally from the pores in the distal end thereof into the interior body wall or tissue without substantial leakage or loss of the medicament at the surface of the body wall.

Various embodiments of the present methods are particularly useful for injecting medicament(s) into an interior body wall or tissue that is subject to motion, for example, the wall of a beating heart during electrophysiologic testing, transmyocardial revascularization, and the like. The blunt cannula reduces incidence of inadvertent puncture and/or prick.

In yet another embodiment, the present invention provides a method for injecting a medicament into tissue in a subject in need thereof comprising: inserting the distal portion of the invention system into the tissue of the subject and causing a therapeutic amount of the medicament to ooze multidirectionally from the distal end into the tissue without substantial damage to the tissue of the subject caused by injectate.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims which come within the meaning and range of equivalency of the claims are to be embraced within their scope, Further, all published documents, patents, and applications mentioned herein are hereby incorporated by reference, as if presented in their entirety herein.

EXAMPLE

FIG. 1 illustrates a neural injection system 1 having a cannula 10, a distal portion 5, shoulder 3, a side port 7, and a stylet (not shown) 2. Cannula 10 is capable of being characterized by a distance from the absolute tip of distal portion 5 to side port 7 and is represented by distance 9. Distance 9 is about 1.1 mm in this embodiment. However, distance 9 is capable of being any distance as dictated by the procedure and/or patient. Distal portion 5 typically comprises a blunt portion 11 and a stylet 2.

A neural injection system 1 of the present invention can be of any length. In various embodiments, the length is the same or similar to that of a 20 or a 22 gauge needle. A 20 gauge needle has an outside diameter of about 0.0355 to 0.0360 mm and an inside diameter of about 0.0230 to 0.0245 mm. A 22 gauge needle has an outside diameter of about 0.0280 to 0.0205 mm and an inside diameter of about 0.0155 to 0.0170 mm.

Figure 2:
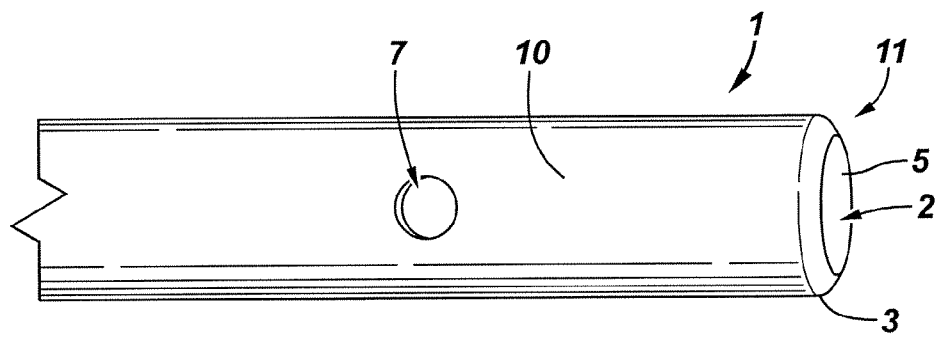
FIG. 2 is an illustration of a distal portion of a blunt needle of a neural injection system of an alternate embodiment of the present invention.

Now referring to FIG. 2, a perspective view of the embodiment of FIG. 1, an arrangement of distal portion 5 becomes more apparent. In this embodiment, distal portion 5 comprises a stylet 2 and blunt portion 11. Shoulder 3 is rounded such that there are no sharp edges. Stylet 2 and shoulder 3 are flush in this embodiment.

Figure 3:
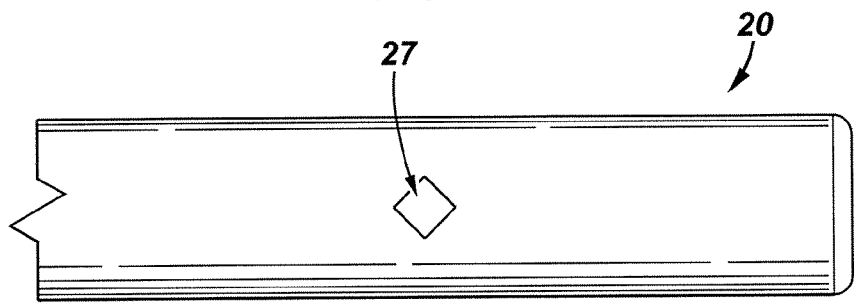
FIG. 3 is an illustration of an alternate embodiment of a distal portion of a blunt needle of a neural injection system of an embodiment of the present invention.

Now referring to FIG. 3, an embodiment of a neural injection system of the present invention is disclosed wherein side port 27 is quadrangular.

Figure 4:
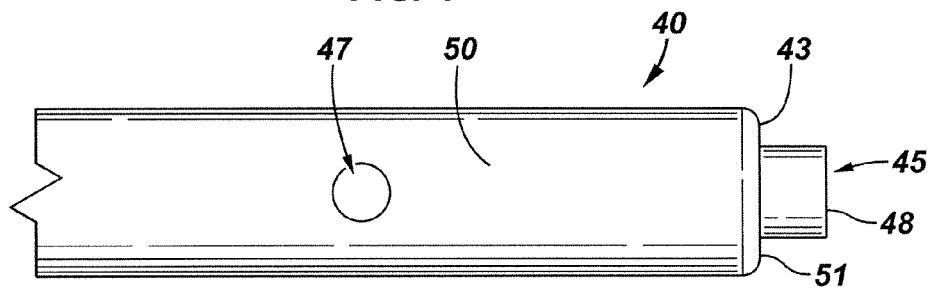
FIG. 4 is an illustration of an alternate embodiment of a distal portion of a blunt needle of a neural injection system of an embodiment of the present invention.

Now referring to FIG. 4, an illustration of an alternate embodiment of a neural injection system of the present invention is disclosed. Neural injection system 40 comprises a distal portion 45, cannula 50, and a circular side port 47, wherein distal portion 45 comprises a shoulder 43, blunt portion 51, and stylet 48. In this embodiment, stylet 48 is not flush with blunt portion 51. Stylet 48 extends past blunt portion 51.

Figure 5:
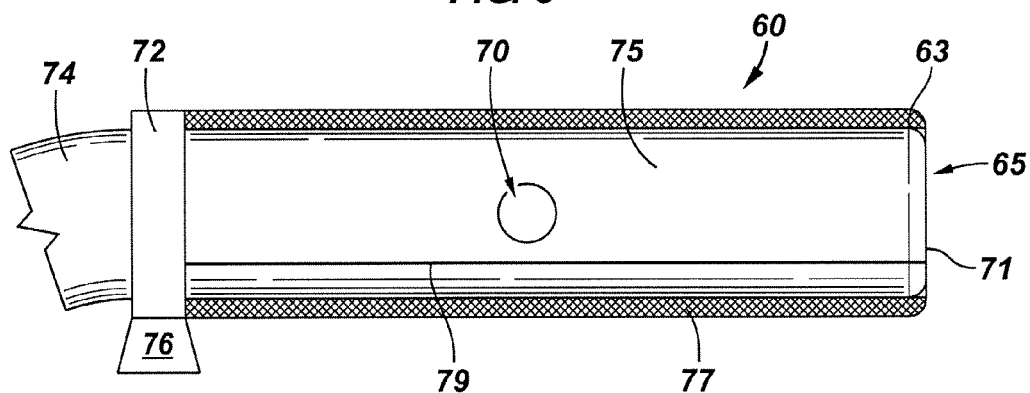
FIG. 5 is an illustration of an alternate embodiment of a blunt needle of the present invention.

Now referring to FIG. 5, an illustration of a cross section of an alternate embodiment of a neural injection system of the present invention is disclosed. Neural Injection System 60 comprises a distal portion 65, a cannula 75, a side port 70, an insulation 77, a wire 79, a connector 72, a wing 76, and a medical instrument 74, wherein distal portion 65 comprises a stylet 71, a shoulder 63, and a blunt portion 71. Wire 79 is capable of treatment of a tissue. Insulation 77 assists in localizing treatment.

Figure 6:
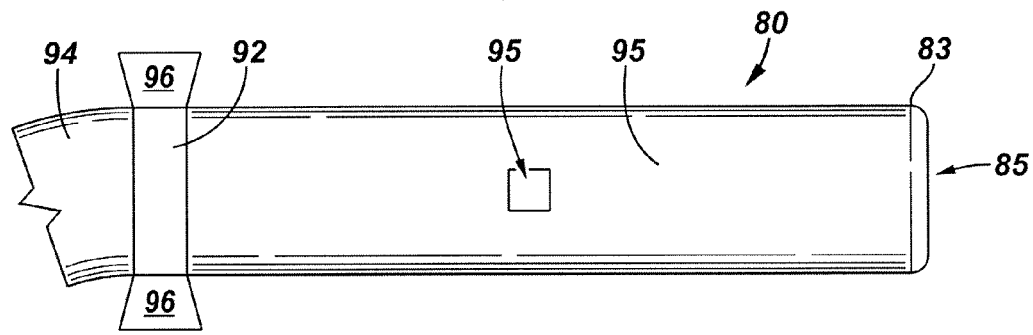
FIG. 6 is an illustration of an alternate embodiment of a blunt needle of the present invention.

Now referring to FIG. 6, an illustration of an alternate embodiment of a neural injection system of the present invention is disclosed. Neural injection system 80 comprises a cannula 95, distal portion 85, a square side port 90, a connector 92, a medical instrument 94, and at least two wings 96.

Figure 7:
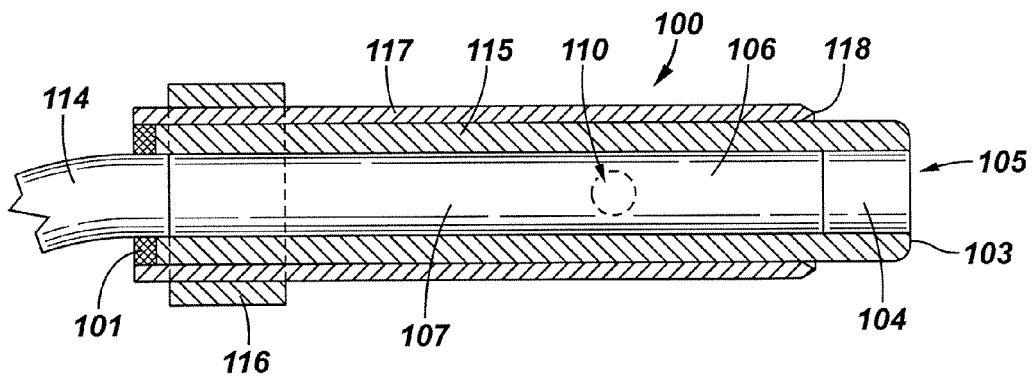
FIG. 7 is an illustration of a cross-section of an alternate embodiment of a blunt needle of the present invention with an incorporated introducer; and, FIG. 8 is an illustration of a cross-section of an alternate embodiment of the present invention wherein the stylet is capable of being used as the introducer.

Now referring to FIG. 7, a cross-section of an alternate embodiment of a neural injection system of the present invention is disclosed. Neural Injection system 100 comprises a distal portion 105, a stylet 107, a cannula 115, an introducer 117, a housing 116, and a medical instrument 114. Distal portion 105 comprises a stylet 107, comprising a solid portion 104 and a generally hollow portion 106.

Side port 110 is not visible in this embodiment, but has been represented by dashed lines for illustration purposes. Side port 110 generally extends across at least cannula 115 and a surface of stylet 107. Therefore, stylet 107 comprises, in application, a side port across cannula 115 and a side port across stylet 107. In various embodiments, the side ports are positioned such that reasonable alignment of the side ports occurs at a desired position of the stylet within the cannula.

Housing 116 is at least partially capable of maintaining introducer 117. FIG. 7 illustrates an at least partially extended introducer 117. Introducer 117 has an edge 118 capable of penetrating a tissue.

Figure 8:
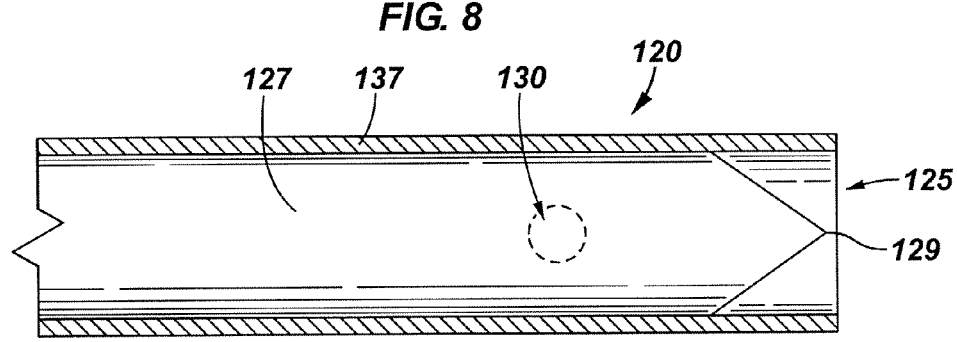

Now referring to FIG. 8, an illustration of a distal portion of an alternate embodiment of a neural injection system of the present invention is disclosed. Neural injection system 120 comprises a cannula 137 and a stylet 127. Side port 130 has been represented by dashed lines for illustrative purposes. In this embodiment, stylet 127 is capable of being extended to contact a tissue wherein point 129 can penetrate the tissue, thereby removing the need for an introducer.

What is claimed is:

1. A method for administering a medicament to a patient comprising the steps of:
    locating a site for injection;
    inserting at least a portion of a neural injection system comprising
    an at least partially hollow cannula being defined by a first inside diameter, a first outside diameter, and a first length,
    a side port located coaxially along the lateral axis of the cannula for fluid communication from inside said at least partially hollow cannula to outside said at least partially hollow cannula, wherein said cannula has a rounded shoulder on an open blunt distal end;
    a stylet, wherein the stylet is capable of being releasably locked in a first position within said cannula; wherein the first position is characterized by the stylet being flush with a shoulder of the rounded open blunt distal end of said cannula; wherein the stylet has an outside diameter that is smaller than the first inside diameter of the cannula; and
    an introducer being defined by a second inside diameter, a second outside diameter, and a second length, wherein the second inside diameter is larger than the first inside diameter of the cannula; and wherein the introducer is used for access across a tissue of a patient that cannot be punctured by the rounded shoulder on the open blunt distal end during a normal insertion procedure; and
    injecting the medicament into the patient.

2. The method of claim 1, wherein injecting the medicament into the patient comprises causing a therapeutic amount of the medicament to ooze multidirectionally from a distal portion of the neural injection system into tissue of the patient.

3. The method of claim 1, further comprising preparing a patient for administering a medicament.

4. The method of claim 3, wherein preparing a patient for administration of a medicament comprises placing the patient's head in a neutral position.

5. The method of claim 1, further comprising stimulating a tissue about the site.

6. The method of claim 5, wherein the step of stimulating said tissue comprises ablating at least a portion of said tissue.

7. The method of claim 1, further comprising the step of probing a tissue.

8. The method of claim 1, wherein the medicament is anesthesia.

9. The method of claim 1, wherein the medicament is injected into a particular tissue of the patient.

10. The method of claim 9, wherein the medicament is injected into an internal organ.

11. The method of claim 10, wherein the medicament is injected into a wall of a beating heart.

12. The method of claim 1, wherein the medicament is a therapeutic agent.

13. The method of claim 1, wherein the medicament is a nucleic acid.

* * * * *